(12) United States Patent
Endo et al.

(10) Patent No.: US 8,249,311 B2
(45) Date of Patent: Aug. 21, 2012

(54) ALCOHOL TEST SYSTEM, ALCOHOL TEST DEVICE, ALCOHOL TEST METHOD, AND PROGRAM

(75) Inventors: Takeshi Endo, Tokyo (JP); Seiichiro Mori, Fukuoka (JP)

(73) Assignee: NEC Corporation, Tokyo (JP)

( * ) Notice: Subject to any disclaimer, the term of this patent is extended or adjusted under 35 U.S.C. 154(b) by 1261 days.

(21) Appl. No.: 11/971,746

(22) Filed: Jan. 9, 2008

(65) Prior Publication Data

US 2008/0170762 A1      Jul. 17, 2008

(30) Foreign Application Priority Data

Jan. 15, 2007 (JP) .................................. 2007-006324

(51) Int. Cl.
   *G06K 9/00* (2006.01)
(52) U.S. Cl. ..................... 382/118; 348/426.1; 382/128
(58) Field of Classification Search .............. 340/426.1, 340/426.2; 382/118, 128
   See application file for complete search history.

(56) References Cited

U.S. PATENT DOCUMENTS

| | | | | |
|---|---|---|---|---|
| 4,916,435 | A * | 4/1990 | Fuller ........................ | 340/573.4 |
| 6,529,617 | B1 * | 3/2003 | Prokoski ..................... | 382/128 |
| 6,748,792 | B1 * | 6/2004 | Freund et al. ................ | 73/23.3 |
| 7,602,948 | B2 * | 10/2009 | Ito ............................ | 382/118 |
| 2006/0009257 | A1 * | 1/2006 | Ku ............................ | 455/556.1 |
| 2011/0292209 | A1 * | 12/2011 | Morley et al. ............... | 348/148 |

FOREIGN PATENT DOCUMENTS

| | | |
|---|---|---|
| JP | 1981049129 B2 | 11/1981 |
| JP | 1986181440 A | 8/1986 |
| JP | 1986185253 A | 8/1986 |
| JP | 1994103430 A | 4/1994 |
| JP | 2003067745 A | 3/2003 |
| JP | 2003228705 A | 8/2003 |
| JP | 2004318411 A | 11/2004 |
| JP | 2005118177 A | 5/2005 |
| JP | 2005157599 A | 6/2005 |
| JP | 2005245956 A | 9/2005 |
| JP | 2005296252 A | 10/2005 |
| JP | 2006026427 A | 2/2006 |
| JP | 2006172375 A | 6/2006 |

OTHER PUBLICATIONS

Japanese Office Action issued Nov. 18, 2008 for JP Application No. 2007-006324.

* cited by examiner

*Primary Examiner* — Gregory M Desire

(57) ABSTRACT

In order to provide an alcohol test device which can keep evidence that an identical person has been surely tested in an alcohol test, the alcohol test device includes an alcohol test unit which measures alcohol concentration from breath exhaled by a subject; a drinking determination unit which determines whether or not the subject is in a drunken state on the basis of a measurement result of the alcohol test unit; a camera unit which photographs a face image of the subject when the breath is exhaled into the alcohol test unit; a face authentication identical person determination unit which compares a face image photographed by the camera unit with a face image of the subject himself (herself) preliminarily photographed, and performs identical person authentication which determines whether or not the subject is the identical person; a result control unit which edits combining a result of identical person authentication by the face authentication identical person determination unit and a result of drinking determination by the drinking determination unit; and a result display unit which displays a result edited by the result control unit.

24 Claims, 11 Drawing Sheets

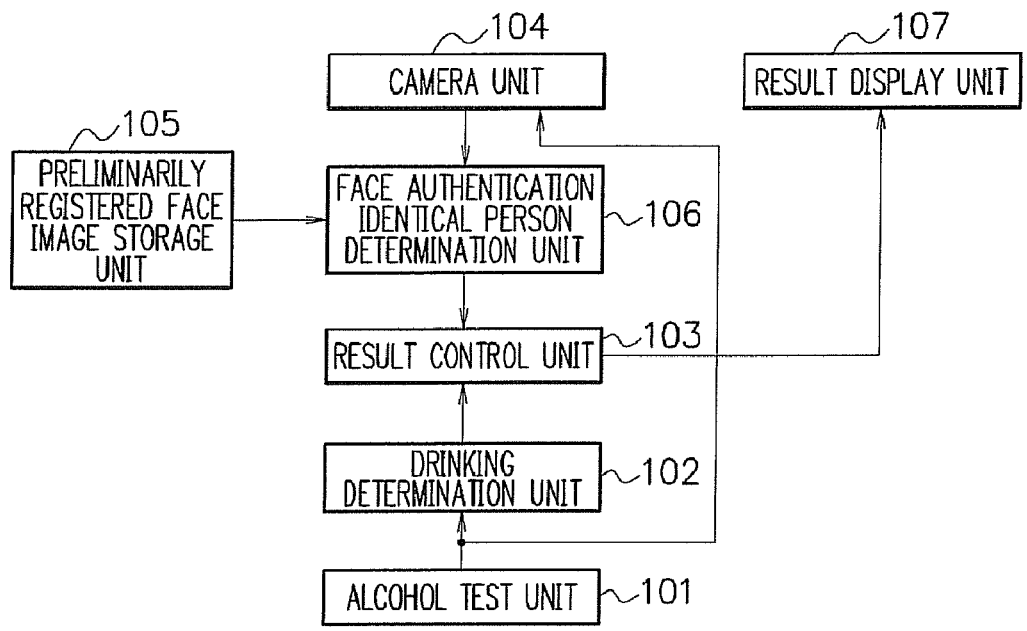
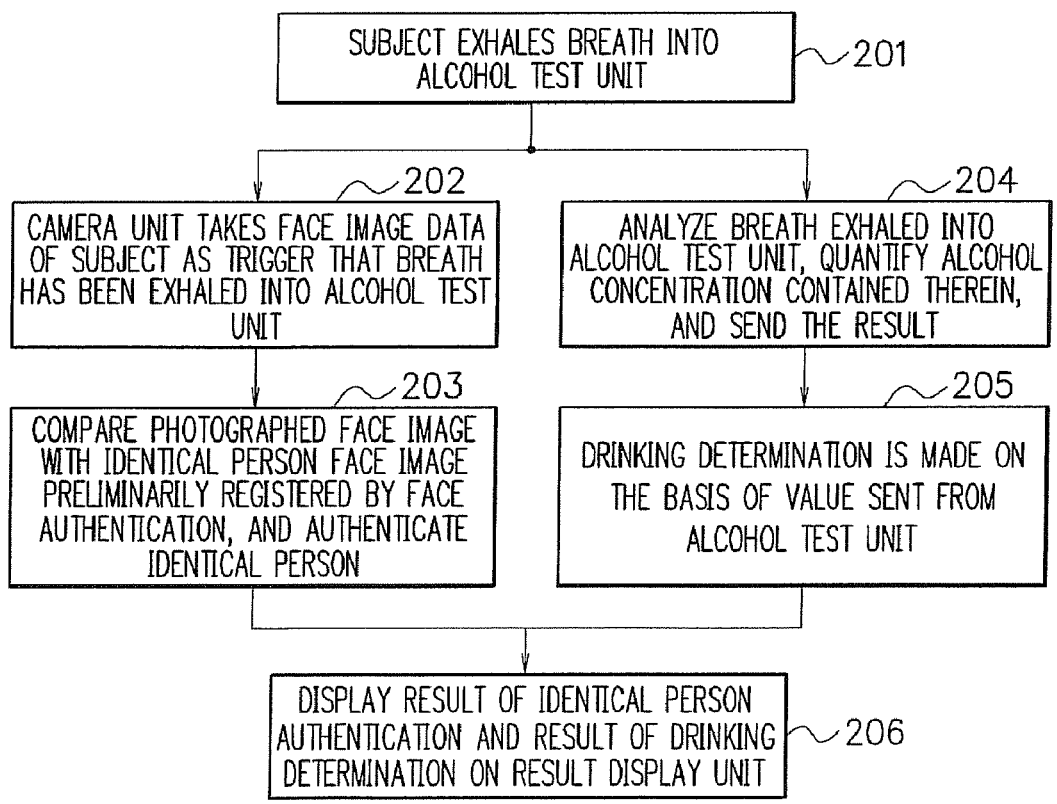

F I G. 6
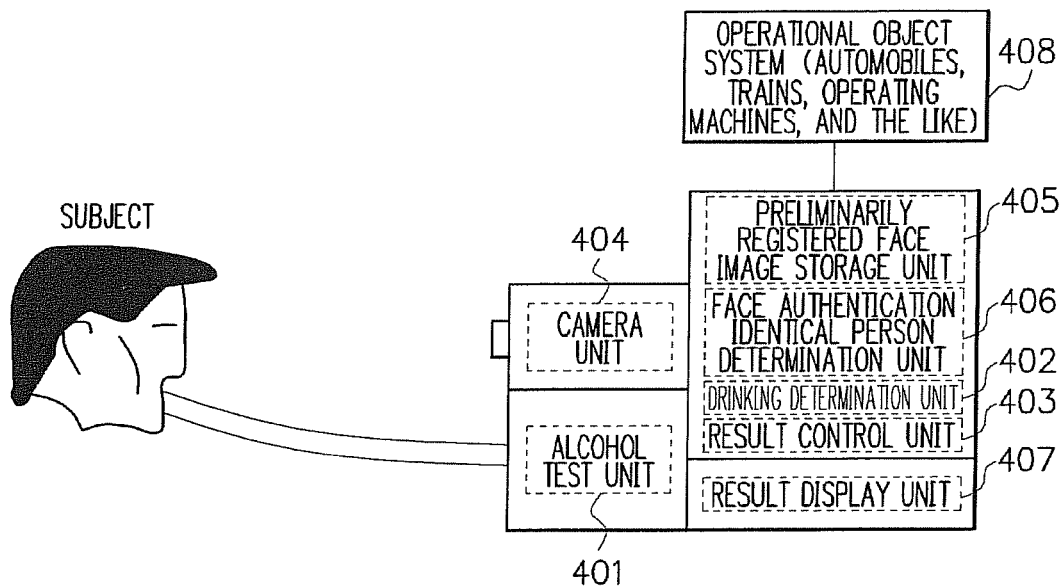
F I G. 7
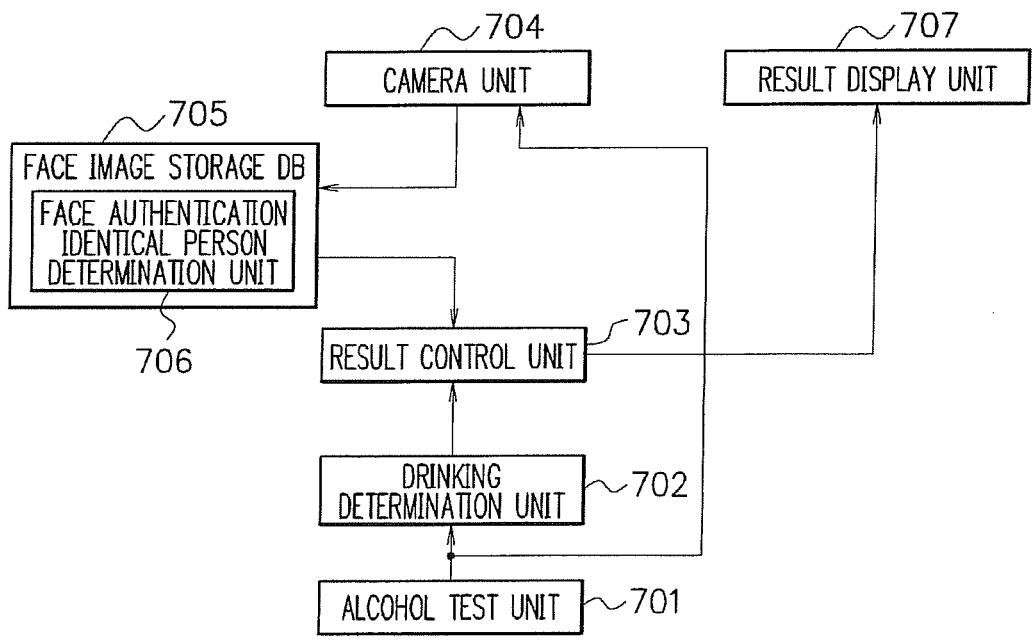

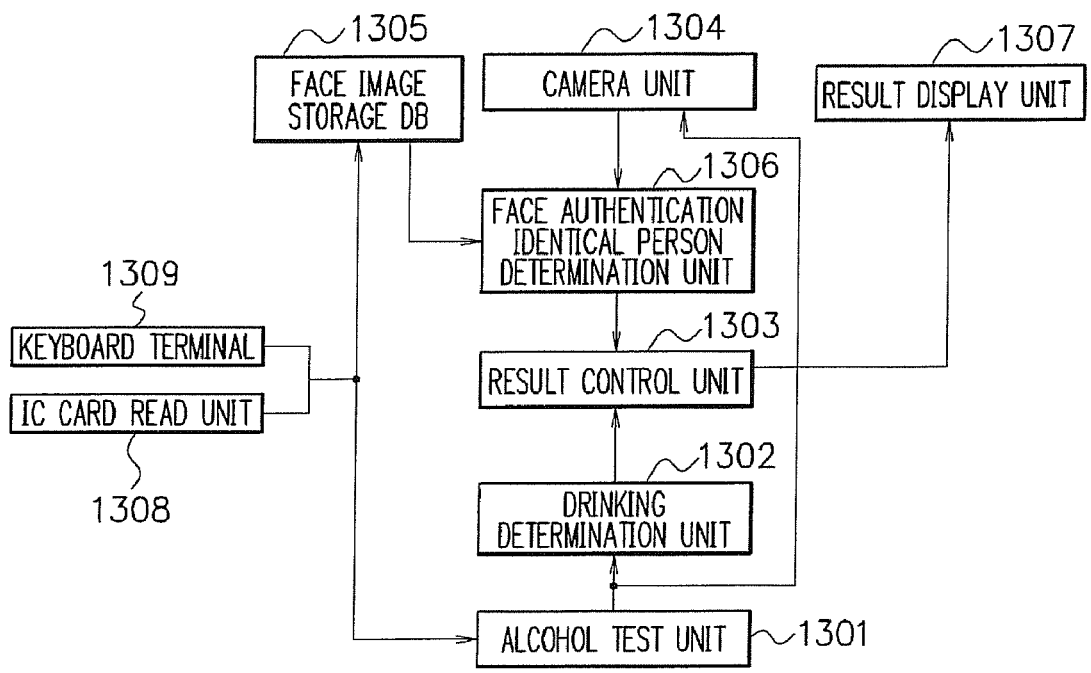
F I G. 13

ALCOHOL TEST SYSTEM, ALCOHOL TEST DEVICE, ALCOHOL TEST METHOD, AND PROGRAM

This application is based upon and claims the benefit of priority from Japanese patent application No. 2007-006324, filed on Jan. 15, 2007, the disclosure of which is incorporated herein in its entirety by reference.

BACKGROUND OF THE INVENTION

1. Field of the Invention

The present invention pertains to an alcohol test system, an alcohol test device, an alcohol test method, and a program, each of which tests alcohol ingested by a person.

2. Description of the Related Art

In recent years, drunk driving by drivers of public buses or trains for example has been increasing and big accidents has been reported. As countermeasures against such cases, an alcohol test instrument system is placed at each business establishment, and a drinking checkup before work is implemented using the system. The alcohol test instrument system is used for a person in a work in which drinking is impermissible in order to test drinking.

In addition, technical documents related to the present invention will be described below.

An "alcohol detection system" disclosed in Japanese Patent Application Laid-Open (JP-A) No. 2005-157599 reads a driver license serving as an authentication of the driver, and a result of an alcohol test is regarded as that of the person.

However, Japanese Patent Application Laid-Open No. 2005-157599 and the alcohol test instrument system have the following problems.

A first problem is that impersonation by others or cheat can be made in such a way that a different person undergoes an alcohol test to escape the test but a true driver goes on duty without undergoing an appropriate alcohol test. This is because the driver license serves as an authentication of the identical person, so that the alcohol test can be asked to others.

A second problem is that evidence of the alcohol test is not kept. This is because an image at a time that a person surely underwent the test is not kept together with data at the time that the test was performed.

SUMMARY OF THE INVENTION

An exemplary object of the present invention is to provide an alcohol test system, an alcohol test device, an alcohol test method, and a program, each of which can keep evidence that an identical person has surely been tested in the alcohol test.

In order to achieve such object, the present invention has the following features.

<Alcohol Test System>

An alcohol test system according to an exemplary aspect of the invention in which an alcohol test device and an external device communicate includes:

an alcohol test unit which measures alcohol concentration from breath exhaled by a subject;

a drinking determination unit which determines whether or not the subject is in a drunken state on the basis of a measurement result of the alcohol test unit;

a camera unit which photographs a face image of the subject when the breath is exhaled into the alcohol test unit, and sends the face image to the external device;

a result control unit which edits combining a result of identical person authentication received from the external device and a result of drinking determination by the drinking determination unit; and a result display unit which displays a result edited by the result control unit, the external device including a face authentication identical person determination unit which compares a face image received from the alcohol test device with a face image of the subject preliminarily photographed and registered, performs authentication which determines whether or not the subject is a same person, and sends a result of the identical person authentication to the alcohol test device.

<Alcohol Test Device>

An alcohol test device according to an exemplary aspect of the invention includes:

an alcohol test unit which measures alcohol concentration from breath exhaled by a subject;

a drinking determination unit which determines whether or not the subject is in a drunken state on the basis of a measurement result of the alcohol test unit;

a camera unit which photographs a face image of the subject when the breath is exhaled into the alcohol test unit;

a face authentication identical person determination unit which compares a face image photographed by the camera unit with a face image of the subject preliminarily photographed, and performs authentication which determines whether or not the subject is a same person;

a result control unit which edits combining a result of authentication by the face authentication identical person determination unit and a result of drinking determination by the drinking determination unit; and a result display unit which displays a result edited by the result control unit.

<Alcohol Test Method>

An alcohol test method according to an exemplary aspect of the invention includes:

an alcohol test step which measures alcohol concentration from breath exhaled by a subject;

a drinking determination step which determines whether or not the subject is in a drunken state on the basis of a measurement result of the alcohol test step;

a photographing step which photographs a face image of the subject when the breath is exhaled at the alcohol test step;

a face authentication identical person determination step which compares a face image photographed at the photograph step with a face image of the subject preliminarily photographed, and performs authentication which determines whether or not the subject is a same person;

a result control step which edits combining a result of authentication by the face authentication identical person determination step and a result of drinking determination by the drinking determination step; and a result display step which displays a result edited by the result control step.

<Program>

A computer-readable medium according to an exemplary aspect of the invention stores a program that causes a computer to perform:

an alcohol test processing which measures alcohol concentration from breath exhaled by a subject;

a drinking determination processing which determines whether or not the subject is in a drunken state on the basis of a measurement result of the alcohol test processing;

a photograph processing which photographs a face image of the subject when the breath is exhaled at the alcohol test processing;

a face authentication identical person determination processing which compares a face image photographed at the photograph processing with a face image of the subject preliminarily photographed, and performs authentication which determines whether or not the subject is a same person;

a result control processing which edits combining a result of authentication by the face authentication identical person determination processing and a result of drinking determination by the drinking determination processing; and a result display processing which displays a result edited by the result control processing.

BRIEF DESCRIPTION OF THE DRAWINGS

Features of the disclosed embodiments will be described by way of the following detailed description with reference to the accompanying drawings in which:

FIG. 1 is a block diagram showing a configuration of an alcohol test device according to a first exemplary embodiment of the present invention;

FIG. 2 is a flowchart showing an operation of the alcohol test device;

FIG. 6 is a diagram showing a state in using the alcohol test device;

FIG. 7 is a block diagram showing a configuration of an alcohol test system (alcohol test device and external device) according to a third exemplary embodiment of the present invention;

FIG. 13 is a block diagram showing a configuration of an alcohol test system (alcohol test device and external device) according to a fifth exemplary embodiment of the present invention;

DESCRIPTION OF EXEMPLARY EMBODIMENTS

Figure 3:
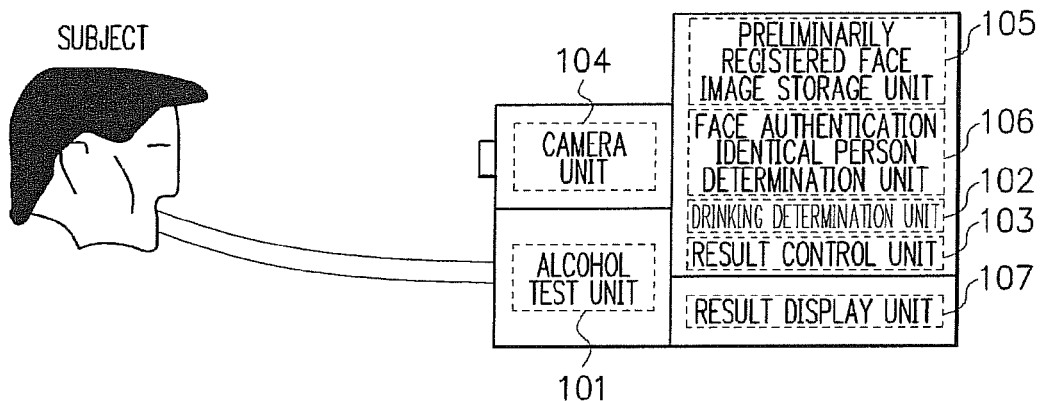
FIG. 3 is a diagram showing a state in using the alcohol test device.

The present invention is characterized in that face image data of a subject is photographed in testing alcohol using both of an alcohol test function and an identical person authentication function, an identical person is authenticated using the face image data, and a result of identical person authentication and a result of an alcohol test are combined. This can specify that the result of the alcohol test has been made for whom, and this can surely prove that the result of the alcohol test is not come from others, but, the alcohol test has been implemented by the identical person; and therefore, it is possible to prevent impersonation by others.

First Exemplary Embodiment

An alcohol test device of a first exemplary embodiment according to the present invention will be described below with reference to FIG. 1.

As shown in FIG. 1, the alcohol test device includes an alcohol test unit 101 which measures alcohol concentration from breath exhaled by a subject; a drinking determination unit 102 which determines whether or not the subject is in a drunken state on the basis of test data (one in which alcohol concentration is quantified) of the alcohol test unit 101; a camera unit 104 which photographs a face image of the subject under test by the alcohol test unit 101; a preliminarily registered face image storage unit 105 in which a face image of the subject photographed before test is preliminarily registered; a face authentication identical person determination unit 106 which compares the face image photographed by the camera unit 104 with the face image preliminarily registered in the preliminarily registered face image storage unit 105, and performs identical person authentication which determines whether or not the subject is a same person; a result control unit 103 which edits a result of identical person authentication and a result of drinking determination; and a result display unit (display) 107 which displays a result edited by the result control unit 103.

An operation of the alcohol test device (one example of an alcohol test method) will be described below with reference to FIGS. 2 and 3. In addition, the operation of the alcohol test device to be described below (one example of the alcohol test method) is executed by that an alcohol test program is read into the alcohol test device and the operation of the alcohol test device is controlled. The alcohol test device executes the following processing by the control of the alcohol test program. This is not limited to the present embodiment; the same is also true in other exemplary embodiments.

In the case where an alcohol test is implemented using the alcohol test device, as shown in FIG. 3, a subject first exhales breath into the alcohol test unit 101 (201).

The breath exhaled into the alcohol test unit 101 becomes a trigger and the camera unit 104 photographs a face image of the subject and obtains the image as face image data (202). The face authentication identical person determination unit 106 associates a face image of a regular user preliminarily registered in the preliminarily registered face image storage unit 105 with a face image of the subject photographed by the camera unit 104, and performs authentication which determines whether or not the subject under test is a same person (203).

On the other hand, in FIG. 2, processes 204 and 205 are performed in parallel with the aforementioned processes 202 and 203. That is, when breath is exhaled into the alcohol test unit 101 by the subject (201), the alcohol test unit 101 analyzes the breath, quantifies alcohol concentration contained in the breath, and sends the result to the drinking determination unit 102 (204). The drinking determination unit 102 determines whether the subject drank alcohol based on a value of the alcohol concentration sent from the alcohol test unit 101 (205).

Then, the result control unit 103 edits a result of authentication at the face authentication identical person determination unit 106 in the aforementioned process 203 and a result of drinking determination at the drinking determination unit 102 in the aforementioned process 205 to be in a combined form, and displays the determination result on the result display unit 107 (206).

As described above, according to the first exemplary embodiment, the following effects are achieved.

A first effect is that it is not possible to implement impersonation or a cheat that a different person undergoes an alcohol test instead of a person concerned. The reason is that a person concerned is identified using a face image photographed at the time of the alcohol test.

A second effect is that it is possible to keep evidence that a same person has been tested. The reason is that face image data of the subject is taken at the time of the alcohol test. Accordingly, the photographed face image becomes evidence.

A third effect is that deceitful conduct is deterred. The reason is that the face image data of the subject is taken at the time of the alcohol test. Accordingly, evidence remains if a dishonest test is done.

Second Exemplary Embodiment

Next, an alcohol test device of a second exemplary embodiment according to the present invention will be described below with reference to FIG. 4.

Figure 4:
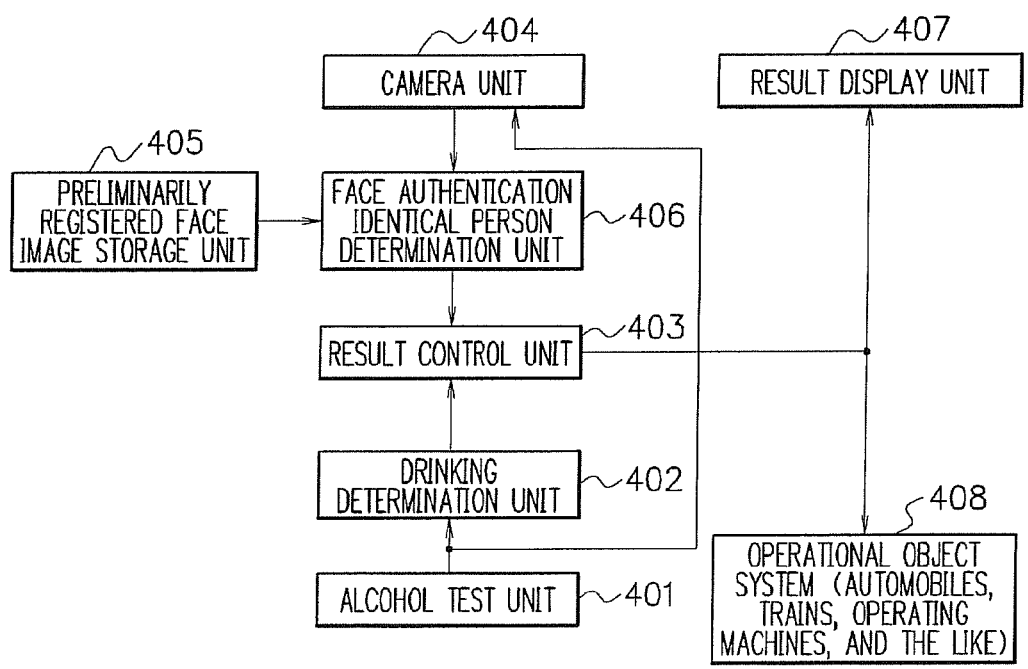
FIG. 4 is a block diagram showing a configuration of an alcohol test device according to a second exemplary embodiment of the present invention.

As shown in FIG. 4, the alcohol test device includes an alcohol test unit 401 which measures alcohol concentration from breath exhaled by a subject; a drinking determination unit 402 which determines whether or not the subject is in a drunken state on the basis of test data (one in which alcohol concentration is quantified) of the alcohol test unit 401; a camera unit 404 which photographs a face image of the subject under test by the alcohol test unit 401; a preliminarily registered face image storage unit 405 in which a face image of the subject photographed before test is preliminarily registered; a face authentication identical person determination unit 406 which compares the face image photographed by the camera unit 404 with the face image preliminarily registered in the preliminarily registered face image storage unit 405, and performs authentication which determines whether or not the subject is a same person; a result control unit 403 which edits a result of authentication and a result of drinking determination, and judges both results and outputs a control signal which controls operation of an operational object system 408 on the basis of the judgment; and a result display unit (display) 407 which displays the results edited by the result control unit 403. The object system 408 is a system that is an object operated by the subject; for example, automobiles, trains, operating machines, and the like.

An operation of the alcohol test device (one example of an alcohol test method) will be described below with reference to FIGS. 5 and 6. In the aforementioned first exemplary embodiment, the results of the authentication and the drinking determination are merely displayed; however, the second exemplary embodiment is different from the first exemplary embodiment in that a control signal which allows or inhibits operation is outputted to the object system 408 in addition to displaying the results of the authentication and the drinking determination in accordance with the results of the result control unit 403 having received the results of the face authentication identical person determination unit 406 and the drinking determination unit 402.

When an alcohol test is performed using the alcohol test device of the second exemplary embodiment, as shown in FIG. 6, a subject first exhales breath into the alcohol test unit 401 (501).

The breath exhaled into the alcohol test unit 401 acts as a trigger of photographing and the camera unit 404 photographs a face image of the subject and acquires as face image data (502). The face authentication identical person determination unit 406 associates a face image of a regular user preliminarily registered in the preliminarily registered face image storage unit 405 with a face image of the subject photographed by the camera unit 404, and performs authentication which determines whether or not the subject under test is a same person (503).

Figure 5:
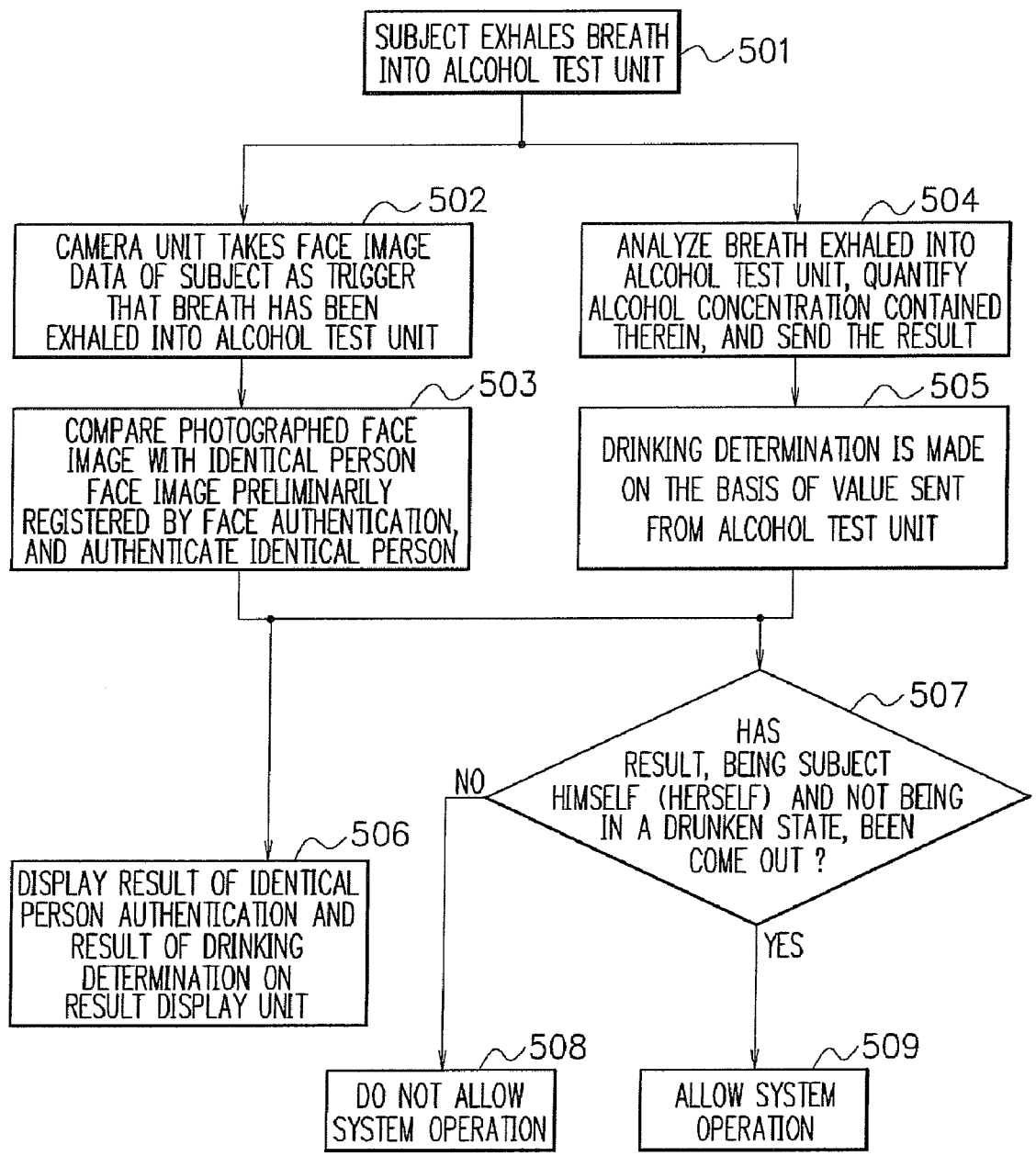
FIG. 5 is a flowchart showing an operation of the alcohol test device.

On the other hand, in FIG. 5, processes 504 and 505 are implemented in parallel with the aforementioned processes 502 and 503. That is, when breath is exhaled into the alcohol test unit 401 by the subject (501), the alcohol test unit 401 analyzes the breath, quantifies alcohol concentration contained in the breath, and sends the result to the drinking determination unit 402 (504). The drinking determination unit 402 determines drinking on the basis of a value of the alcohol concentration sent from the alcohol test unit 401 (505).

Then, the result control unit 403 edits a result of authentication at the face authentication identical person determination unit 406 in the aforementioned process 503 and a result of drinking determination at the drinking determination unit 402 in the aforementioned process 505 to be in a combined form, and displays the determination result on the result display unit 407 (506).

Furthermore, as the results of the authentication and the drinking determination, the result control unit 403 judges whether or not a result, "being the subject himself/herself and not being in a drunken state", has come out (507). When it is judged that "the result of the identical person authentication identifies the subject as a same person and the result of the drinking determination is not in a drunken state (507/YES)," the result control unit 403 outputs a control signal which allows operation of the operational object system 408 (509). On the other hand, when it is judged that "the result of the identical person authentication does not identify the subject as himself/herself or the result of the drinking determination is in a drunken state (a state where a certain amount of alcohol more than a fixed value is detected) (507/NO)," the result control unit 403 outputs a control signal which inhibits operation of the object system 408 (508).

As described above, according to the second exemplary embodiment, a function which transmits a control signal that controls availability of operation in an object system such as automobiles, trains, operating machines, and the like is provided. Accordingly, it is possible to control whether to allow operation of the object system when there is no problem in both the drinking determination and the identical person authentication. At the same time, it is possible to control whether to inhibit operation of the object system when a drunken state and/or impersonation by others are detected.

Third Exemplary Embodiment

Next, an alcohol test system (alcohol test device and external device) of a third exemplary embodiment according to the present invention will be described below with reference to FIG. 7.

As shown in FIG. 7, the alcohol test device of the third exemplary embodiment includes an alcohol test unit 701 which measures alcohol concentration from breath exhaled by a subject; a drinking determination unit 702 which determines whether or not the subject is in a drunken state on the basis of test data (one in which alcohol concentration is quantified) of the alcohol test unit 701; a camera unit 704 which photographs a face image of the subject under test by the alcohol test unit 701; a result control unit 703 which edits a result of identification authentication and a result of drinking determination; and a result display unit (display) 707 which displays a result edited by the result control unit 703. Furthermore, the alcohol test device of the third exemplary embodiment can communicate with a database server (face image storage DB 705 shown in the present embodiment) that is one example of the external device via a communication interface (not shown in the drawing).

The third exemplary embodiment is an example which uses the face image storage DB 705 that is a database server (external device) that can store large volume of data and is provided outside the alcohol test device in place of the preliminarily registered face image storage unit 105 provided in the alcohol test device in the first exemplary embodiment. In the face image storage DB 705, a face image of the subject photographed before test is preliminarily registered as in the preliminarily registered face image storage unit 105. Furthermore, the face image storage DB 705 can communicate with the alcohol test device via a communication interface (not shown in the drawing); and has a face authentication identical person determination unit 706 which receives the face image photographed by the camera unit 704 from the alcohol test device, compares the received face image with the face image preliminarily registered in the face image storage DB 705, and performs identical person authentication which determines whether or not the subject is a same person.

That is, in the third exemplary embodiment, the alcohol test device and the external device (face image storage DB 705) form the alcohol test system. Then, the following operation will be performed in the alcohol test system.

An operation of the alcohol test system of the third exemplary embodiment of the present invention (one example of an alcohol test method) will be described below with reference to FIGS. 8 and 9.

Figure 9:
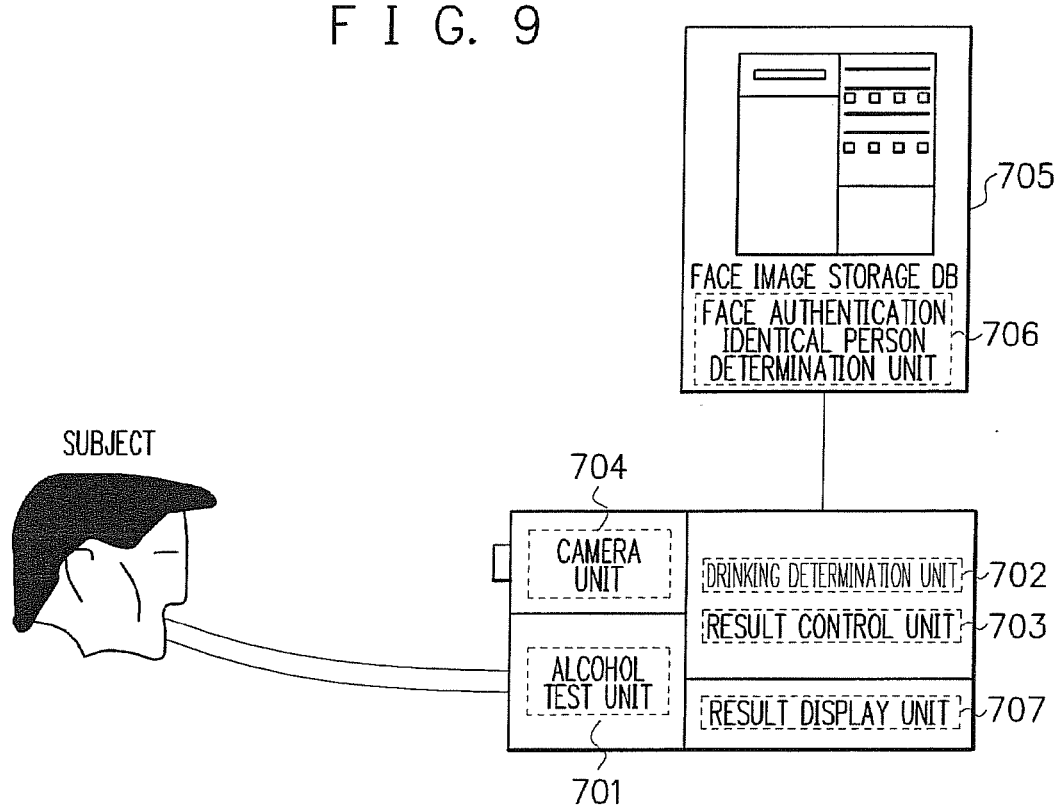
FIG. 9 is a diagram showing a state in using the alcohol test system (alcohol test device and external device)

When an alcohol test is implemented using the alcohol test device of the third exemplary embodiment, as shown in FIG. 9, a subject first exhales breath into the alcohol test unit 701 (801).

The breath exhaled into the alcohol test unit 701 acts as a trigger and the camera unit 704 photographs a face image of the subject and acquires as face image data (802). The camera unit 704 sends face image data acquired via a communication interface (not shown in the drawing) to the face authentication identical person determination unit 706 in the face image storage DB 705 (803). The face authentication identical person determination unit 706 collates the face image of a regular user preliminarily registered in the face image storage DB 705 with the face image of the subject photographed by the camera unit 704 and received from the alcohol test device, and performs identification authentication which determines whether or not the subject under test is a same person (804). After that, the face authentication identical person determination unit 706 sends a result of the authentication to the result control unit 703 of the alcohol test device.

Figure 8:
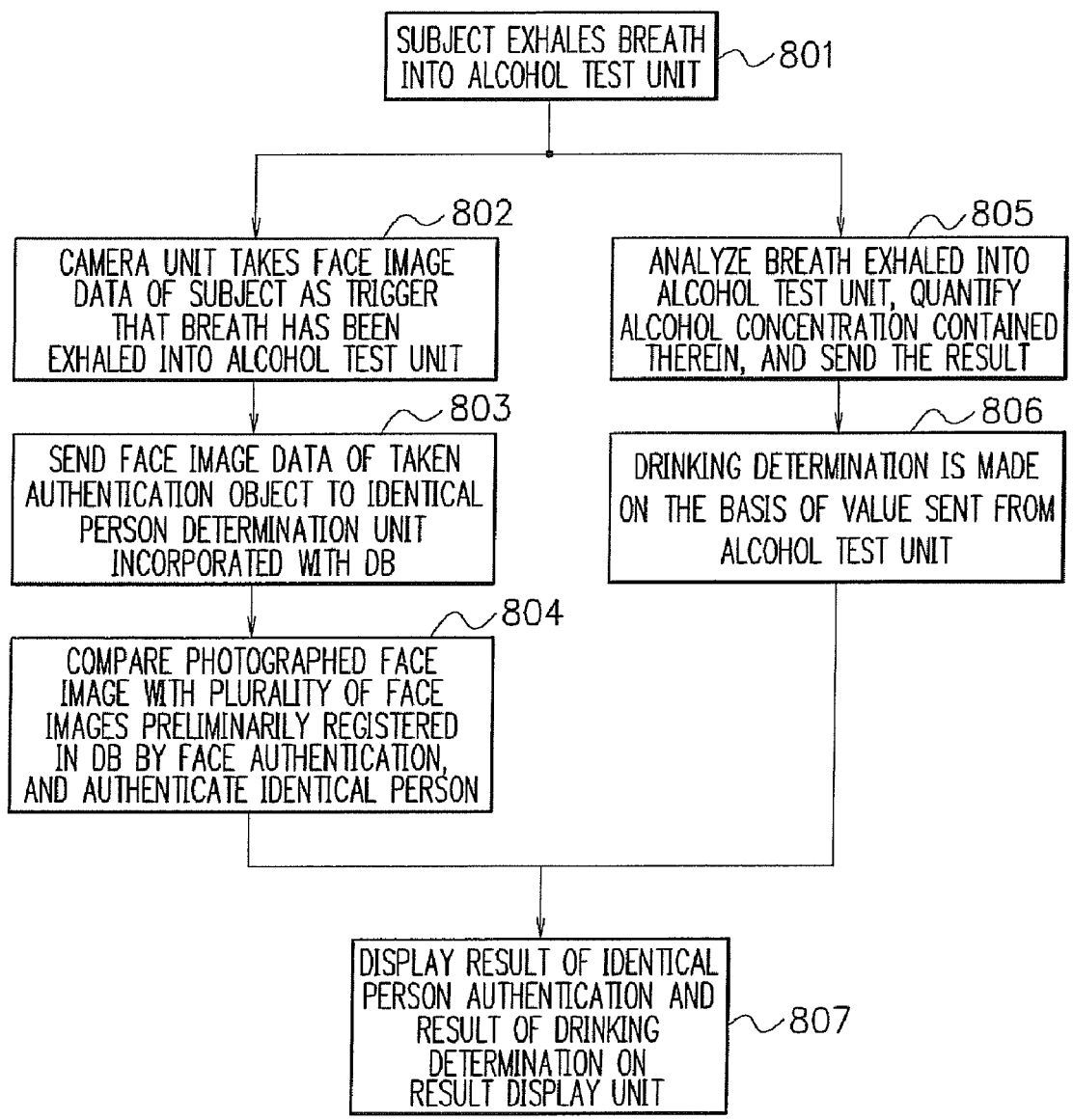
FIG. 8 is a flowchart showing an operation of the alcohol test system (alcohol test device and external device)

On the other hand, in FIG. 8, the processes 805 and 806 are implemented in parallel with the aforementioned processes 802, 803, and 804. That is, when breath is exhaled into the alcohol test unit 701 by the subject (801), the alcohol test unit 701 analyzes the breath, quantifies alcohol concentration contained in the breath, and sends the result to the drinking determination unit 702 (805). The drinking determination unit 702 determines whether the subject has drunk alcohol on the basis of a value of the alcohol concentration sent from the alcohol test unit 701 (806).

Then, the result control unit 703 receives the result of identical person authentication at the face authentication identical person determination unit 706 in the aforementioned process 804 from the face authentication identical person determination unit 706, edits the received result of the identical person authentication and the result of drinking determination at the drinking determination unit 702 in the aforementioned process 806 to be in a combined form, and displays the determination result on the result display unit 707 (807).

As described above, according to the third exemplary embodiment, the identical person authentication is not implemented on the alcohol test device side, but, a person is authenticated by the database server (face image storage DB); and therefore, it is effective in the case of using the alcohol test device by a plurality of subjects.

In addition, in the third exemplary embodiment, in FIGS. 7 and 9, it is configured that the face authentication identical person determination unit is not provided on the alcohol test device side. However, the face authentication identical person determination unit may be provided in the alcohol test device as shown in FIGS. 1 and 3 of the first exemplary embodiment. In this case, it is preferable to be able to arbitrarily choose which to use, the face authentication identical person determination unit 706 in the face image storage DB 705 or the face authentication identical person determination unit provided in the alcohol test device.

In addition, in the third exemplary embodiment, only the results of the authentication and the drinking determination are displayed as shown in FIG. 8. However, it may be made so as to implement control of the object system, combined with the configuration of the second exemplary embodiment.

Fourth Exemplary Embodiment

An alcohol test device of a fourth exemplary embodiment according to the present invention will be described below with reference to FIG. 10.

Figure 10:
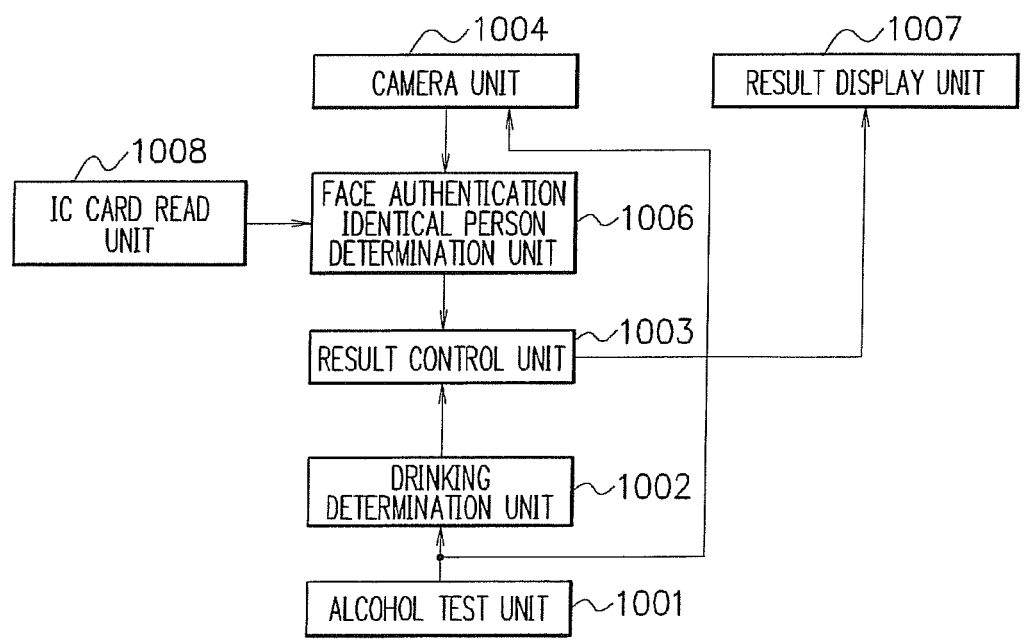
FIG. 10 is a block diagram showing a configuration of an alcohol test device according to a fourth exemplary embodiment of the present invention.

As shown in FIG. 10, the alcohol test device of the fourth exemplary embodiment includes an alcohol test unit 1001 which measures alcohol concentration from breath exhaled by a subject; a drinking determination unit 1002 which determines whether or not the subject is in a drunken state on the basis of test data (one to which alcohol concentration is quantified) of the alcohol test unit 1001; a camera unit 1004 which photographs a face image of the subject under test by the alcohol test unit 1001; a face authentication identical person determination unit 1006 which compares the face image photographed by the camera unit 1004 with the face image preliminarily registered in a preliminarily registered face image storage unit 1005, and performs authentication which determines whether or not the subject is a same person; a result control unit 1003 which edits a result of the authentication and a result of drinking determination; a result display unit (display) 1007 which displays a result edited by the result control unit 1003; and an IC card read unit 1008 which reads data stored in an IC card (storage medium).

The IC card read unit 1008 is provided as shown in FIG. 10 in place of the preliminarily registered face image storage unit 105 provided in the alcohol test device in the first exemplary embodiment, and reads the face image data by the IC card read unit 1008 from the IC card in which the preliminarily registered face image is stored.

An operation of the alcohol test device of the fourth exemplary embodiment according to the present invention (one example of an alcohol test method) will be described below with reference to FIGS. 11 and 12.

Figure 12:
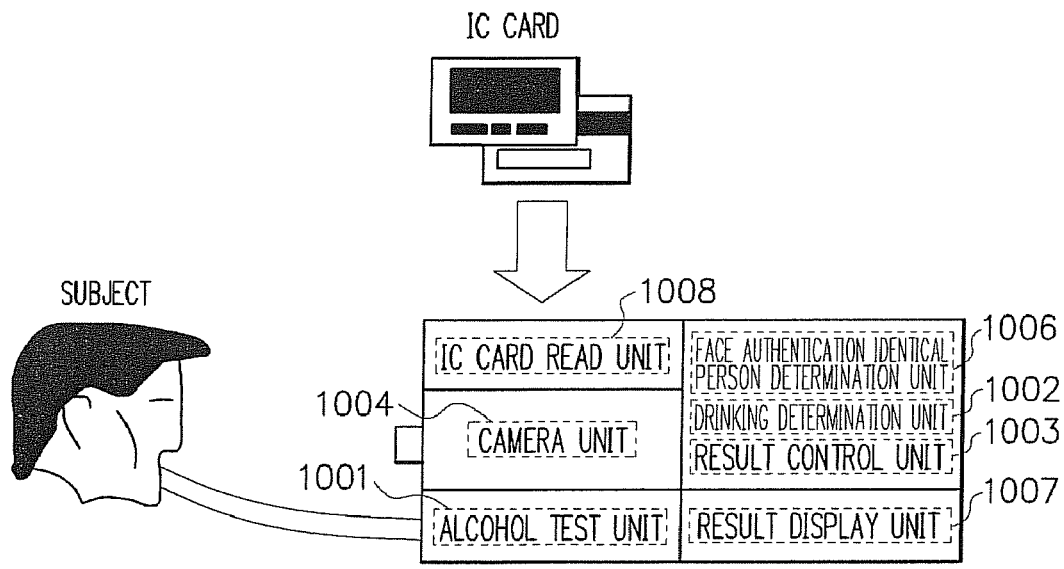
FIG. 12 is a diagram showing a state in using the alcohol test device.

When an alcohol test is implemented using the alcohol test device of the fourth exemplary embodiment, as shown in FIG. 12, a subject first puts an IC card on the IC card read unit 1008 to make the IC card read unit 1008 read face image data of the relevant subject preliminarily stored in the IC card (1101). Then, the subject exhales breath into the alcohol test unit 1001 (1102).

The breath is exhaled into the alcohol test unit 1001 becomes a trigger and the camera unit 1004 photographs a face image of the subject and acquires the image as face image data (1103). The face authentication identical person determination unit 1006 collates the face image of the relevant subject read from the IC card by the IC card read unit 1008 with the face image of the subject photographed by the camera unit 1004, and performs identification authentication, which determines whether or not the subject under test, is a same person (1104).

Figure 11:
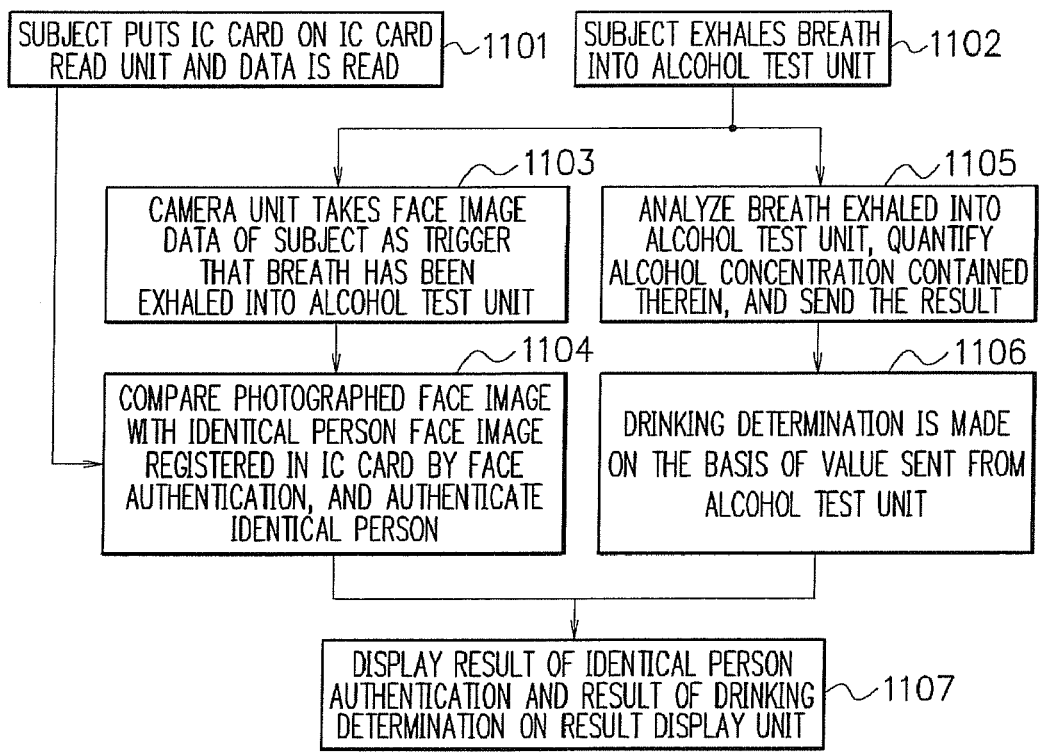
FIG. 11 is a flowchart showing an operation of the alcohol test device.

On the other hand, in FIG. 11, processes 1105 and 1106 are implemented in parallel with the aforementioned processes 1103 and 1104. That is, when breath is exhaled into the alcohol test unit 1001 by the subject (1102), the alcohol test unit 1001 analyzes the breath, quantifies alcohol concentration contained in the breath, and sends the result to the drinking determination unit 1002 (1105). The drinking determination unit 1002 determines whether the subject has drunk alcohol based on a value of the alcohol concentration sent from the alcohol test unit 1001 (1106).

Then, the result control unit 1003 edits a result of the authentication at the face authentication identical person determination unit 1006 in the aforementioned process 1104 and a result of drinking determination at the drinking determination unit 1002 in the aforementioned process 1106 to be in a combined form, and displays the determination result on the result display unit 1007 (1107).

As described above, according to the fourth exemplary embodiment, the face image of each subject is acquired from the IC card. Therefore, a preliminarily registered face image storage unit need not be provided in the alcohol test device, and it is effective in the case where many subjects use the device.

In addition, the fourth exemplary embodiment can be configured and operated by combining at least one of the first to third embodiments. For example, in addition to the fourth exemplary embodiment, there may be made such that the preliminarily registered face image storage unit is provided in the alcohol test device as described in the first exemplary embodiment, it may be made possible to communicate with the face image storage DB as described in the third exemplary embodiment, or it may be made possible to control operation of the object system as described in the second exemplary embodiment.

Furthermore, as shown in FIG. 12, the fourth exemplary embodiment is configured so that the IC card read unit 1008 is provided in the alcohol test device. However, the IC card read unit 1008 may be configured so as to be able to connect to an outside IC card read unit (read device) via an interface.

Fifth Exemplary Embodiment

Next, a configuration of an alcohol test system (alcohol test device and external device) of a fifth exemplary embodiment according to the present invention will be described below with reference to FIG. 13.

As shown in FIG. 13, the alcohol test device of the fifth exemplary embodiment includes an alcohol test unit 1301 which measures alcohol concentration from breath exhaled by a subject; a drinking determination unit 1302 which determines whether or not the subject is in a drunken state on the basis of test data (quantified alcohol concentration) of the alcohol test unit 1301; a camera unit 1304 which photographs a face image of the subject under test by the alcohol test unit 1301; a face authentication identical person determination unit 1306 which compares the face image photographed by the camera unit 1304 with the preliminarily registered face image received from the face image storage DB 1305, and performs authentication which determines whether or not the subject is a same person; a result control unit 1303 which edits a result of the authentication and a result of drinking determination; and a result display unit (display) 1307 which displays a result edited by the result control unit 1303. Furthermore, the alcohol test device of the fifth exemplary embodiment can communicate with a database server (face image storage DB 1305 shown in the present embodiment) that is one example of the external device via a communication interface (not shown in the drawings).

The fifth exemplary embodiment is an example which uses the face image storage DB 1305 that is a database server that can store large volume of data and is provided outside the alcohol test device in place of the preliminarily registered face image storage unit 105 provided in the alcohol test device in the first exemplary embodiment. In the face image storage DB 1305, a face image of the subject photographed before test is preliminarily registered as in the preliminarily registered face image storage unit 105. Furthermore, the face image storage DB 1305 can communicate with the alcohol test device via a communication interface (not shown in the drawing), and sends preliminarily registered face image data to the face authentication identical person determination unit 1306 on the alcohol test device side. In addition, as shown in FIGS. 13 and 15, the face image storage DB 1305 is connected to an IC card read unit 1308 and a keyboard terminal 1309 via an interface (not shown in the drawing).

That is, in the fifth exemplary embodiment, the alcohol test device and the external device (face image storage DB 1305) forms the alcohol test system. Then, the following operation will be performed in the alcohol test system.

An operation of the alcohol test device that is the fifth exemplary embodiment of the present invention (one example of an alcohol test method) will be described below with reference to FIGS. 14 and 15.

Figure 15:
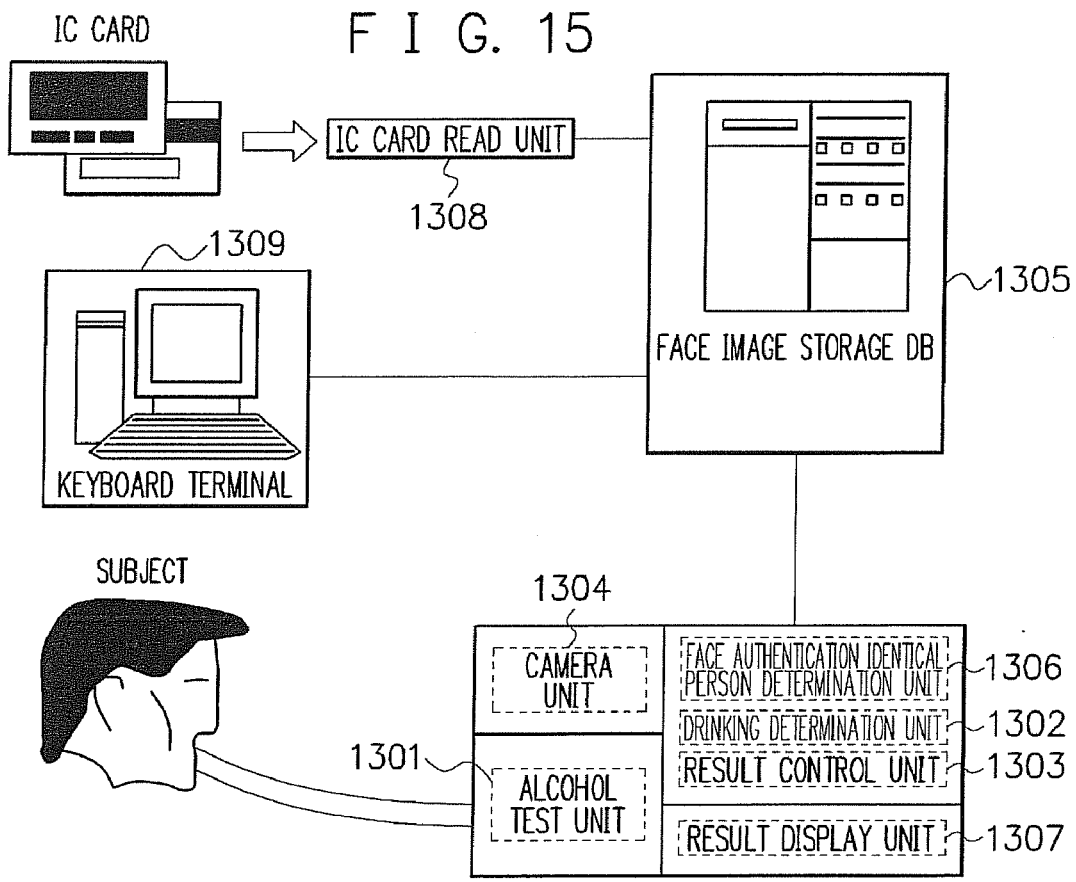
FIG. 15 is a diagram showing a state in using the alcohol test system (alcohol test device and external device)

When an alcohol test is implemented using the alcohol test device of the fifth exemplary embodiment, as shown in FIG. 15, for example, a subject first puts an IC card on the IC card read unit 1308 to make the IC card read unit 1308 read the relevant subject ID (one example of identification information) preliminarily stored in the IC card (1401). Furthermore, the subject inputs a unique password (one example of identification information) from the keyboard terminal 1309 (1402). In this case, the face image storage DB 1305 searches ID read by IC card read unit 1308 and face image data associated with the password inputted from the keyboard terminal 1309 from among a plurality of preliminarily registered face image data, and sends the searched face image data to the face authentication identical person determination unit 1306 of the alcohol test device.

When breath is exhaled into the alcohol test unit 1301 by the subject (1403), the breath exhaled into the alcohol test unit 1301 becoming a trigger, the camera unit 1304 photographs a face image of the subject and acquires as face image data (1404). The face authentication identical person determination unit 1306 collates the face image of the relevant subject received from the face image storage DB 1305 with the face image of the subject photographed by the camera unit 1304, and performs authentication which determines whether or not the subject under test is a same person (1405).

Figure 14:
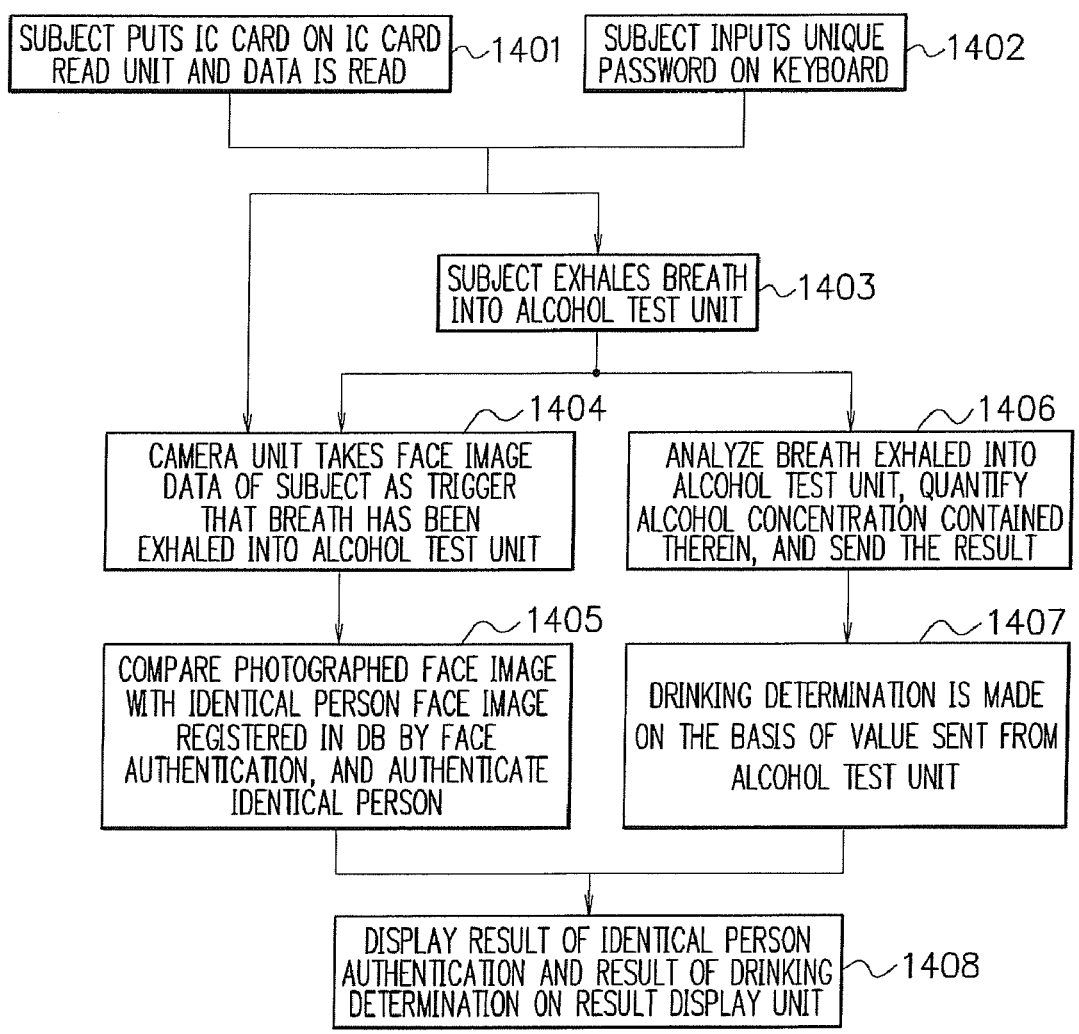
FIG. 14 is a flowchart showing an operation of the alcohol test system (alcohol test device and external device)

On the other hand, in FIG. 14, processes 1406 and 1407 are implemented in parallel with the aforementioned processes 1404 and 1405. That is, when breath is exhaled into the alcohol test unit 1301 by the subject (1403), the alcohol test unit 1301 analyzes the breath, quantifies alcohol concentration contained in the breath, and sends the result to the drinking determination unit 1302 (1406). The drinking determination unit 1302 determines whether the subject has drunk alcohol on the basis of a value of the alcohol concentration sent from the alcohol test unit 1301 (1407).

Then, the result control unit 1303 edits a result of the authentication at the face authentication identical person determination unit 1306 in the aforementioned process 1405 and a result of drinking determination at the drinking determination unit 1302 in the aforementioned process 1407 to be in a combined form, and displays the determination result on the result display unit 1307 (1408).

As described above, according to the fifth exemplary embodiment, the face image of each subject is acquired from the face image storage DB; and therefore, a preliminarily registered face image storage unit need not be provided in the alcohol test device, and it is effective in the case where many subjects use the device.

In addition, the fifth exemplary embodiment can be configured and operated by combining at least one of the first to fourth exemplary embodiments.

Sixth Exemplary Embodiment

A configuration of an alcohol test device of a sixth exemplary embodiment according to the present invention will be described below with reference to FIG. 16.

Figure 16:
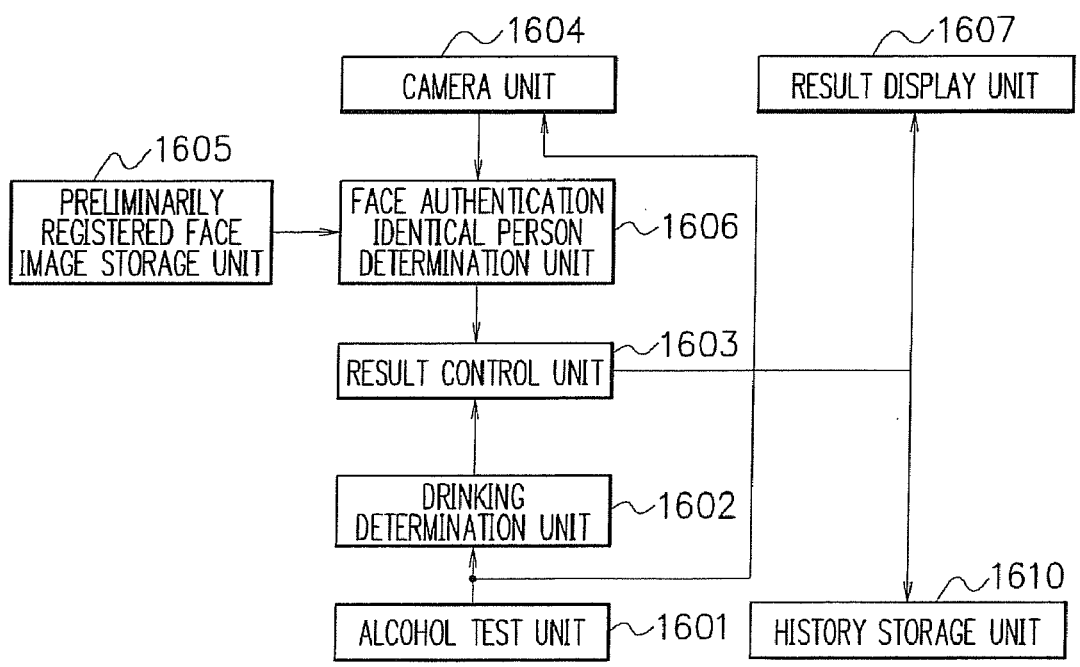
FIG. 16 is a block diagram showing a configuration of an alcohol test device according to a sixth exemplary embodiment of the present invention.

As shown in FIG. 16, the alcohol test device of the sixth exemplary embodiment includes an alcohol test unit 1601 which measures alcohol concentration from breath exhaled by a subject; a drinking determination unit 1602 which determines whether or not the subject is in a drunken state on the basis of test data (one to which alcohol concentration is quantified) of the alcohol test unit 1601; a camera unit 1604 which photographs a face image of the subject under test by the alcohol test unit 1601; a preliminarily registered and face image storage unit 1605 in which a face image of the subject photographed prior to test is preliminarily registered; a face authentication identical person determination unit 1606 which compares the face image photographed by the camera unit 1604 with the face image preliminarily registered in the preliminarily registered face image storage unit 1605, and performs authentication which determines whether or not the subject is a same person; a result control unit 1603 which edits a result of the authentication and a result of drinking determination; a result display unit (display) 1607 which displays a result edited by the result control unit 1603; and a history storage unit 1610 which stores history information that shows an alcohol test has been implemented.

An operation of the alcohol test device of the sixth exemplary embodiment according to the present invention (one example of an alcohol test method) will be described below with reference to FIGS. 17 and 18.

Figure 18:
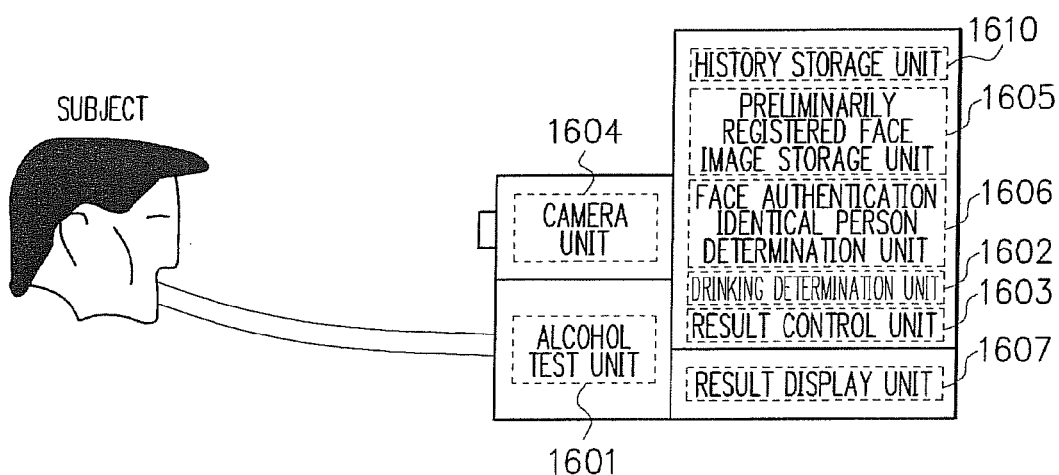
FIG. 18 is a diagram showing a state in using the alcohol test device.

When an alcohol test is implemented using the alcohol test device of the sixth exemplary embodiment, as shown in FIG. 18, the subject exhales breath into the alcohol test unit 1601 (1701).

The breath exhaled into the alcohol test unit 1601 acting as a trigger, the camera unit 1604 photographs a face image of the subject and acquires as face image data (1702). The face authentication identical person determination unit 1606 collates the face image of a regular user preliminarily registered in the preliminarily registered face image storage unit 1605 with the face image of the subject photographed by the camera unit 1604, and performs authentication which determines whether or not the subject under test is a same person (1703).

Figure 17:
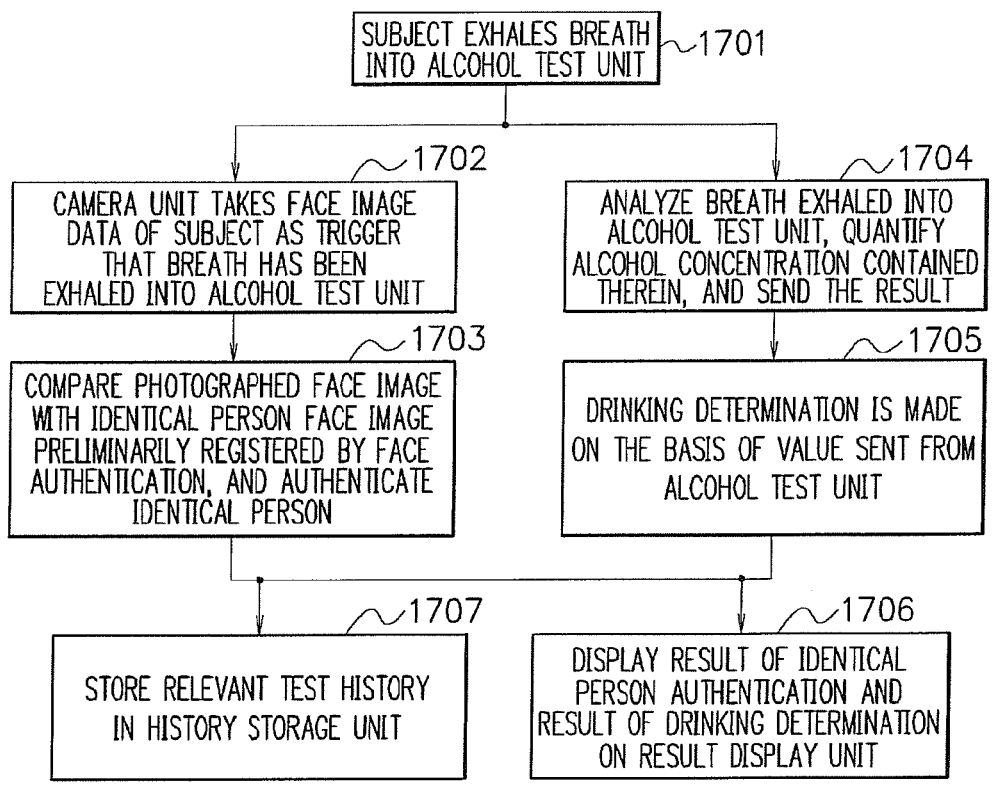
FIG. 17 is a flowchart showing an operation of the alcohol test device.

On the other hand, in FIG. 17, processes 1704 and 1705 are implemented in parallel with the aforementioned processes 1702 and 1703. That is, when breath is exhaled into the alcohol test unit 1601 by the subject (1701), the alcohol test unit 1601 analyzes the breath, quantifies alcohol concentration contained in the breath, and sends the result to the drinking determination unit 1602 (1704). The drinking determination unit 1602 determines drinking based on a value of the alcohol concentration sent from the alcohol test unit 1601 (1705).

Then, the result control unit 1603 edits a result of authentication at the face authentication identical person determination unit 1606 in the aforementioned process 1703 and a result of drinking determination at the drinking determination unit 1602 in the aforementioned process 1705 to be in a combined form, and displays the determination result on the result display unit 1607 (1706).

Furthermore, the result control unit 1603 stores history information that shows the relevant alcohol test has been implemented in the history storage unit 1610 (1707). The history information to be stored is edited in the result control unit 1603; and the contents is that, for example, date when test is performed (date and time when breath is exhaled into the alcohol test unit) is associated with the aforementioned result of authentication and result of drinking determination. The history information stored in the history storage unit 1610 can be displayed on the result display unit 1607.

As described above, according to the sixth exemplary embodiment, history that shows the alcohol test has been implemented can be stored; and therefore, evidence that shows who and when underwent the test can be kept.

In addition, in the sixth exemplary embodiment, the history storage unit is configured to be mounted in the alcohol test device; however, it may be configured that the history storage unit is mounted on an external computer (for example, the face image storage DB or the like described in the third and fifth exemplary embodiments) connected by a local area network (referred to as LAN) or a wide area network (referred to as WAN), and the history is sent from the alcohol test device via a communication interface and stored in the external computer or the like. Furthermore, the history may be stored in the history storage unit in the inside of the alcohol test device; and is sent via a communication interface and stored in the external computer or the like.

In addition, the sixth exemplary embodiment can be configured and operated by combining at least one of the first to fifth exemplary embodiments.

The above described respective embodiments are exemplary embodiments of the present invention. The present invention is not limited to the aforementioned respective embodiments. A person skilled in the art may perform modifications and substitutions of the aforementioned embodiments without deviating from the scope of technical idea of the present invention, and embodiments with various changes can be constructed. In addition, each of the first to sixth embodiments can be configured and operated, being arbitrarily combined within a possible range.

For example, the control operation for the alcohol test device in the above described embodiments can also be executed using hardware, software, or a composite configuration of both.

In addition, when the processing is executed using software, it is possible to execute by installing a program recorded with a process sequence in a memory in a computer incorporated in hardware for exclusive use. Alternatively, it is possible to execute by installing a program in a general-purpose computer in which various processing are executable.

For example, the program can be preliminarily recorded in a hard disk and/or a read only memory (referred to as ROM) serving as a recording medium. Alternatively, the program can be temporarily or permanently stored (recorded) in a removable recording medium. Such removable recording medium can be provided as a so-called "package software." In addition, as a removable recording medium, a compact disc read only memory (referred to as CD-ROM), a magneto-optical disc (referred to as MO), a digital versatile disc (referred to as DVD), a magnetic disc, a semiconductor memory can be used.

In addition, the program is installed from such above described removable recording medium to a computer. Furthermore, the program is transferred wirelessly from a download site to a computer. In addition, the program is transferred by wire to a computer via a network.

Furthermore, the alcohol test device in the embodiments can be constructed so as not only to be executed in temporal sequence in accordance with processing operations described in the aforementioned embodiments, but also to be executed in parallel or individually according to throughput of a device executing processing if necessary.

By the description of the above embodiments, the present invention has the following features.

A first alcohol test system of the present invention is an alcohol test system in which an alcohol test device and an external device communicate, the alcohol test device including:

an alcohol test unit which measures alcohol concentration from breath exhaled by a subject;

a drinking determination unit which determines whether or not the subject is in a drunken state on the basis of a measurement result of the alcohol test unit;

a camera unit which photographs a face image of the subject when the breath is exhaled into the alcohol test unit, and sends the face image to the external device;

a result control unit which edits combining a result of authentication received from the external device and a result of drinking determination by the drinking determination unit; and a result display unit which displays a result edited by the result control unit, the external device including a face authentication identical person determination unit which compares a face image received from the alcohol test device with a face image of the subject preliminarily photographed and registered, performs authentication which determines whether the subject is a same person, and sends a result of the authentication to the alcohol test device.

Consequently, according to the first alcohol test system of the present invention, an identical person is authenticated using a face image photographed at the same time as an alcohol test; and therefore, it is not possible to implement impersonation or a cheat that a different person undergoes the alcohol test instead of the same person.

Furthermore, according to the first alcohol test system of the present invention, face image data of the subject is taken at the same time as the alcohol test so that the photographed face image becomes evidence. Therefore, it is possible to keep evidence that the same person has been tested.

Still furthermore, according to the first alcohol test system of the present invention, the face image data of the subject is taken at the same time as the alcohol test so that such evidence that someone tried cheating remains. Therefore, suppression effect of dishonest conduct is achieved.

Further, according to the first alcohol test system of the present invention, the same person is authenticated on the external device side; and therefore, it is effective in the case of using the alcohol test device by many people.

Still further, according to the first alcohol test system of the present invention, a face image of each subject preliminarily registered in the external device is used; and therefore, a memory or the like which stores such face images need not be provided in the alcohol test device, and it is effective in the case where many subjects use the device.

A second alcohol test system of the present invention is that, in the first alcohol test system of the present invention, when the result of the authentication indicates that the subject is a same person, and the result of the drinking determination is not in a drunken state, the result control unit outputs a control signal which allows the subject to operate an object system; and when the result of the authentication indicates that the subject is not a same person, or the result of the drinking determination is in a drunken state, the result control unit outputs a control signal which inhibits the subject from operating the object system.

Consequently, according to the second alcohol test system of the present invention, a function which transmits a control signal that controls availability of operation in an object system such as automobiles, trains, operating machines, and the like is provided. Accordingly, it is possible to control operation of the object system when there is no problem in both the drinking determination and the authentication; and at the same time, it is possible to inhibit operation of the operational object system when a drunken state and/or impersonation by others are detected.

A third alcohol test system of the present invention is that, in the first alcohol test system of the present invention, at least one of the alcohol test device and the external device further includes a history storage unit which stores history information in which date and time when the breath was exhaled into the alcohol test unit is associated with the result of the authentication and the result of the drinking determination.

Consequently, according to the third alcohol test system of the present invention, history that shows the alcohol test has been implemented can be stored. Therefore, evidence that shows who and when underwent the test can be kept.

A first alcohol test device of the present invention includes:

an alcohol test unit which measures alcohol concentration from breath exhaled by a subject;

a drinking determination unit which determines whether or not the subject is in a drunken state on the basis of a measurement result of the alcohol test unit;

a camera unit which photographs a face image of the subject when the breath is exhaled into the alcohol test unit;

a face authentication identical person determination unit which compares a face image photographed by the camera unit with a face image of the subject preliminarily photographed (for example, a face image preliminarily registered in a preliminarily registered face image storage unit in the alcohol test device after preliminarily being photographed), and performs authentication which determines whether or not the subject is a same person;

a result control unit which edits combining a result of authentication by the face authentication identical person determination unit and a result of drinking determination by the drinking determination unit; and a result display unit which displays a result edited by the result control unit.

Consequently, according to the first alcohol test device of the present invention, a person is authenticated using a face image photographed at the same time as an alcohol test. Therefore, it is not possible to implement impersonation or a cheat that another person undergoes the alcohol test instead of the original person.

Furthermore, according to the first alcohol test device of the present invention, face image data of the subject is taken at the same time as the alcohol test, accordingly, the photographed face image becomes evidence. Therefore, it is possible to keep evidence that the same person has been tested.

Further, according to the first alcohol test device of the present invention, the face image data of the subject is taken at the same time as the alcohol test. Accordingly, evidence is kept even when malicious conduct is made; and therefore, suppression effect of dishonest operation is achieved.

A second alcohol test device of the present invention, in the first alcohol test device of the present invention, further includes a storage medium read unit which reads a face image from a storage medium in which the face image of the subject preliminarily photographed is preliminarily registered, and the face authentication identical person determination unit compares the face image photographed by the camera unit with the face image read by the storage medium read unit, and performs authentication which determines whether or not the subject is a same person.

Consequently, according to the second alcohol test device of the present invention, a face image of each subject is acquired from a storage medium such as an IC card; therefore, a preliminarily registered face image storage unit need not be provided in the alcohol test device, and it is effective in the case where many subjects use the device.

A third alcohol test device of the present invention, in the alcohol test device of the present invention, further includes an interface which can communicate with an external device in which the face image of the subject preliminarily photographed is preliminarily registered, and the face authentication identical person determination unit compares the face image photographed by the camera unit with the face image received from the external device, and performs authentication which determines whether or not the subject is a same person.

Consequently, according to the third alcohol test device of the present invention, a face image of each subject preliminarily registered in an external device is used; and therefore, a preliminarily registered face image storage unit does not need to be provided in the alcohol test device, and it is effective in the case where many subjects use the device.

A fourth alcohol test device of the present invention is that, in the first alcohol test device of the present invention, when the result of the identical person authentication is the subject and the result of the drinking determination is not in a drunken state, the result control unit outputs a control signal which allows the subject to operate an object system; and when the result of the identical person authentication indicates that the subject is not a same person, or the result of the drinking determination is in a drunken state, the result control unit outputs a control signal which inhibits the subject from operating the operational object system.

Consequently, according to the fourth alcohol test device of the present invention, a function which transmits a control signal that controls availability of operation in an operational object system such as automobiles, trains, operating machines, and the like is provided; accordingly, it is possible to enable operation of the object system when there is no problem in both the drinking determination and the authentication; and at the same time, it is possible to inhibit operation of the operational object system when a drunken state and/or impersonation by others are detected.

A fifth alcohol test device of the present invention, in the first alcohol test device of the present invention, further includes a history storage unit which stores history information in which date and time when the breath was exhaled into the alcohol test unit is associated with the result of the authentication and the result of the drinking determination.

Consequently, according to the fifth alcohol test device of the present invention, history that shows the alcohol test has been implemented can be stored; therefore, evidence that shows who and when underwent the test can be kept.

A sixth alcohol test device of the present invention is that, in the fifth alcohol test device of the present invention, the result control unit sends out the history information in which the date and time when the breath was exhaled into the alcohol test unit is associated with the result of the authentication and the result of the drinking determination.

Consequently, according to the sixth alcohol test device of the present invention, history that shows an alcohol test has been implemented (being evidence that shows who and when underwent the test) can be stored in an external device.

A first alcohol test method of the present invention includes performing:

an alcohol test step which measures alcohol concentration from breath exhaled by a subject;

a drinking determination step which determines whether or not the subject is in a drunken state on the basis of a measurement result of the alcohol test step;

a photograph step which photographs a face image of the subject when the breath is exhaled at the alcohol test step;

a face authentication identical person determination step which compares a face image of the subject photographed at the photograph step with a face image of the subject preliminarily photographed, and performs authentication which determines whether or not the subject is a same person;

a result control step which edits combining a result of authentication by the face authentication identical person determination step and a result of drinking determination by the drinking determination step; and a result display step which displays a result edited by the result control step.

In addition, it may perform a preliminarily registered face image storage step in which the face image of the subject preliminarily photographed is preliminarily registered before the face authentication identical person determination step.

Consequently, according to the first alcohol test method of the present invention, a same person is authenticated using a face image photographed at the same time as an alcohol test; therefore, it is not possible to implement impersonation or a cheat that a different person undergoes the alcohol test instead of the original person.

Furthermore, according to the first alcohol test method of the present invention, face image data of the subject is taken at the same time as the alcohol test. Accordingly, the photographed face image becomes evidence; therefore, it is possible to keep evidence that the same person has been tested.

Further, according to the first alcohol test method of the present invention, the face image data of the subject is taken at the same time as the alcohol test. Accordingly, evidence is kept when cheating is intended; and therefore, suppression effect of dishonest operation is achieved.

A second alcohol test method of the present invention, in the first alcohol test method of the present invention, further performs a storage medium read step which reads a face image from a storage medium in which the face image of the subject preliminarily photographed is preliminarily registered, and the face authentication identical person determination step compares the face image photographed at the photograph step with the face image read at the storage medium read step, and performs authentication which determines whether or not the subject is a same person.

Consequently, according to the second alcohol test method of the present invention, a face image of each subject is acquired from a storage medium such as an IC card; and therefore, a preliminarily registered face image storage unit need not be provided in the alcohol test device, and it is effective in the case where many subjects use the device.

A third alcohol test method of the present invention, in the first alcohol test method of the present invention, further performs communication with an external device in which the face image of the subject preliminarily photographed is preliminarily registered, and the face authentication identical person determination step compares the face image photographed by the photograph step with the face image received from the external device, and performs authentication which determines whether or not the subject is a same person.

Consequently, according to the third alcohol test method of the present invention, a face image of each subject preliminarily registered in an external device is used; and therefore, a preliminarily registered face image storage unit needs not be provided in the alcohol test device, and it is effective in the case where many subjects use the device.

A fourth alcohol test method of the present invention is that, in the first alcohol test method of the present invention, when the result of the identical person authentication indicates that the subject is a same person, and the result of the drinking determination is not in a drunken state, the result control step outputs a control signal which allows the subject to operate an object system; and when the result of the identical person authentication is not the subject or the result of the drinking determination is in a drunken state, the result control step outputs a control signal which inhibits operation of the subject to the operational object system.

Consequently, according to the fourth alcohol test method of the present invention, a function which transmits a control signal that controls availability of operation in an object system such as automobiles, trains, operating machines, and the like is provided; accordingly, it is possible to control so as to enable operation of the operational object system when there is no problem in both the drinking determination and the authentication; and at the same time, it is possible to inhibit operation of the object system when a drunken state and/or impersonation by others are detected.

A fifth alcohol test method of the present invention, in the first alcohol test method of the present invention, further includes a history storage step which stores history information in which date and time when breath is exhaled at the alcohol test step corresponds to the result of the authentication and the result of the drinking determination.

Consequently, according to the fifth alcohol test method of the present invention, history that shows the alcohol test has been implemented can be stored; and therefore, evidence that shows who and when underwent the test can be kept.

A sixth alcohol test method of the present invention, in the fifth alcohol test method of the present invention, the result control step sends out the history information in which the date and time when the breath was exhaled at the alcohol test step corresponds to the result of the authentication and the result of drinking determination.

Consequently, according to the sixth alcohol test method of the present invention, history that shows the alcohol test has been implemented (being evidence that shows who and when underwent the test) can be stored in an external device.

A first computer-readable medium of the present invention storing a program causes a computer to perform:

an alcohol test processing which measures alcohol concentration from breath exhaled by a subject;

a drinking determination processing which determines whether or not the subject is in a drunken state on the basis of a measurement result of the alcohol test processing;

a photograph processing which photographs a face image of the subject when the breath is exhaled at the alcohol test processing;

a face authentication identical person determination processing which compares a face image photographed at the photograph processing with a face image of the subject preliminarily photographed, and performs authentication which determines whether or not the subject is a same person;

a result control processing which edits combining a result of authentication by the face authentication identical person determination processing and a result of drinking determination by the drinking determination processing; and a result display processing which displays a result edited by the result control processing.

In addition, it may make a computer execute a preliminarily registered face image storage processing in which the face image of the subject preliminarily photographed is preliminarily registered before the face authentication identical person determination processing.

Consequently, according to the first computer-readable medium storing a program of the present invention, a same person is authenticated using a face image photographed at the same time as an alcohol test; and therefore, it is not possible to implement impersonation or cheat that a different person undergoes the alcohol test instead of the same person.

Furthermore, according to the first computer-readable medium storing a program of the present invention, face image data of the subject is taken at the same time as the alcohol test, accordingly, the photographed face image becomes evidence; and therefore, it is possible to keep evidence that the same person has been tested.

Further, according to the first computer-readable medium storing a program of the present invention, the face image data of the subject is taken at the same time as the alcohol test. Accordingly, evidence is kept when cheating is intended; and therefore, suppression effect of dishonest operation is achieved.

A second computer-readable medium storing a program of the present invention causes the computer to perform:

a storage medium read processing which reads a face image from a storage medium in which the face image of the subject preliminarily photographed is preliminarily registered, and the face authentication identical person determination processing compares the face image photographed at the photograph processing with the face image read at the storage medium read processing, and a processing which determines whether or not the subject is a same person.

Consequently, according to the second computer-readable medium storing a program of the present invention, a face image of each subject is acquired from a storage medium such as an IC card; and therefore, a preliminarily registered face image storage unit needs not be provided in the alcohol test device, and it is effective in the case where many subjects use the device.

A third computer-readable medium storing a program of the present invention, further causes the computer to perform a communication processing which communicates with an external device in which the face image of the subject preliminarily photographed is preliminarily registered, and the face authentication identical person determination processing compares the face image photographed at the photograph processing with the face image received from the external device, and a processing which determines whether or not the subject is a same person.

Consequently, according to the third computer-readable medium storing a program of the present invention, a face image of each subject preliminarily registered in an external device is used; and therefore, a preliminarily registered face image storage unit need not be provided in the alcohol test device, and it is effective in the case where many subjects use the device.

A fourth computer-readable medium storing a program of the present invention is that, in the first program of the present invention, when the result of the identical person authentication is the subject and the result of the drinking determination is not in a drunken state, the result control processing outputs a control signal which allows operation of the subject to an operational object system which is an object operated by the subject; and when the result of the identical person authentication is not the subject or the result of the drinking determination is in a drunken state, the result control processing outputs a control signal which inhibits the subject from operating the operational object system.

Consequently, according to the fourth computer-readable medium storing a program of the present invention, a function which transmits a control signal that controls availability of operation in an object system such as automobiles, trains, operating machines, and the like is provided; accordingly, it is possible to enable operation of the object system when there is no problem in both the drinking determination and the authentication; and at the same time, it is possible to inhibit operation of the object system when a drunken state and/or impersonation by others are detected.

A fifth computer-readable medium storing a program of the present invention further causes the computer to perform a history storage processing which stores history information in which date and time when the breath was exhaled at the alcohol test processing is associated with the result of the authentication and the result of the drinking determination.

Consequently, according to the fifth computer-readable medium storing a program of the present invention, history that shows the alcohol test has been implemented can be stored; and therefore, evidence that shows who and when underwent the test can be kept.

A sixth computer-readable medium storing a program of the present invention causes the computer to perform a processing to send out the history information in which the date and time when the breath was exhaled at the alcohol test processing corresponds to the result of the authentication and the result of the drinking determination.

Consequently, according to the sixth computer-readable medium storing a program of the present invention, history that shows the alcohol test has been implemented (being evidence that shows who and when underwent the test) can be stored in an external device.

The present invention can be applied to a device, equipment, system, method, and program which are used for specifying a subject when a predetermined component such as alcohol is detected from a human body or the like.

While the invention has been particularly shown and described with reference to exemplary embodiments thereof, the invention is not limited to these embodiments. It will be understood by those of ordinary skill in the art that various changes in form and details may be made therein without departing from the spirit and scope of the present invention as defined by the claims.

What is claimed is:

1. An alcohol test system in which an alcohol test device and an external device communicate, wherein
the alcohol test device comprises:
an alcohol test unit which measures alcohol concentration from breath exhaled by a subject;
a drinking determination unit which determines whether or not the subject is in a drunken state on the basis of a measurement result of the alcohol test unit;
a camera unit which photographs a face image of the subject by using a trigger that the breath is exhaled into the alcohol test unit such that the face image is photographed responsive to and as a result of exhaling of the breath into the alcohol test unit, and sends the face image to the external device;
a result control unit which edits combining a result of authentication received from the external device and a result of drinking determination by the drinking determination unit; and
a result display unit which displays a result edited by the result control unit,
the external device including a face authentication identical person determination unit which compares a face image received from the alcohol test device with a face image of the subject preliminarily photographed and registered, performs authentication which determines whether the subject is a same person, and sends a result of the authentication to the alcohol test device.

2. The alcohol test system of claim 1,
wherein, when the result of the authentication indicates that the subject is a same person, and the result of the drinking determination is not in a drunken state, the result control unit outputs a control signal which allows the subject to operate an object system; and
wherein, when the result of the authentication indicates that the subject is not a same person, or the result of the drinking determination is in a drunken state, the result control unit outputs a control signal which inhibits the subject from operating the object system.

3. The alcohol test system of claim 1,
wherein at least one of the alcohol test device and the external device further comprises a history storage unit which stores history information in which a date and time when the breath was exhaled into the alcohol test unit is associated with the result of the authentication and the result of the drinking determination.

4. An alcohol test device, comprising:
an alcohol test unit which measures alcohol concentration from breath exhaled by a subject;

a drinking determination unit which determines whether the subject is in a drunken state based on a measurement result of the alcohol test unit;

a camera unit which photographs a face image of the subject by using a trigger that the breath is exhaled into the alcohol test unit such that the face image is photographed responsive to and as a result of exhaling of the breath into the alcohol test unit;

a face authentication identical person determination unit which compares a face image photographed by the camera unit with a face image of the subject preliminarily photographed, and performs authentication which determines whether the subject is a same person;

a result control unit which edits combining a result of authentication by the face authentication identical person determination unit and a result of drinking determination by the drinking determination unit; and a result display unit which displays a result edited by the result control unit.

5. The alcohol test device of claim 4, further comprising a preliminarily registered face image storage unit in which the face image of the subject preliminarily photographed is registered.

6. The alcohol test device of claim 4, further comprising a storage medium read unit which reads a face image from a storage medium in which the face image of the subject preliminarily photographed is registered, and wherein the face authentication identical person determination unit compares the face image photographed by the camera unit with the face image read by the storage medium read unit, and performs authentication which determines whether the subject is a same person.

7. The alcohol test device of claim 4, further comprising an interface which communicates with an external device in which the face image of the subject preliminarily photographed is registered, and wherein the face authentication identical person determination unit compares the face image photographed by the camera unit with the face image received from the external device, and performs authentication which determines whether the subject is a same person.

8. The alcohol test device of claim 4, wherein, when the result of the identical person authentication indicates that the subject is a same person, and the result of the drinking determination is not in a drunken state, the result control unit outputs a control signal which allows the subject to operate an object system; and wherein, when the result of the identical person authentication indicates that the subject is not a same person, or the result of the drinking determination is in a drunken state, the result control unit outputs a control signal which inhibits the subject from operating the object system.

9. The alcohol test device of claim 4, further comprising a history storage unit which stores history information in which a date and time when the breath was exhaled into the alcohol test unit is associated with the result of the authentication and the result of the drinking determination.

10. The alcohol test device of claim 9, wherein the result control unit sends out the history information in which the date and time when the breath was exhaled into the alcohol test unit is associated with the result of the authentication and the result of the drinking determination.

11. An alcohol test method, comprising:

an alcohol testing, performed by an alcohol test device, which measures alcohol concentration from breath exhaled by a subject;

a drinking determination, performed by the alcohol test device, which determines whether the subject is in a drunken state on the basis of a measurement result of the alcohol testing;

a photographing, performed by the alcohol test device, which photographs a face image of the subject by using a trigger that the breath is exhaled at the alcohol testing such that the face image is photographed responsive to and as a result of exhaling of the breath at the alcohol test;

a face authentication identical person determination, performed by the alcohol test device, which compares a face image photographed at the photographing with a face image of the subject preliminarily photographed, and performs authentication which determines whether the subject is a same person;

a result controlling, performed by the alcohol test device, which edits combining a result of authentication by the face authentication identical person determination and a result of drinking determination by the drinking determination; and a result displaying, performed by the alcohol test device, which displays a result edited by the result controlling.

12. The alcohol test method of claim 11, further comprising performing a preliminarily registered face image storage in which the face image of the subject preliminarily photographed is registered.

13. The alcohol test method of claim 11, further comprising performing a storage medium reading which reads a face image from a storage medium in which the face image of the subject preliminarily photographed is registered, and wherein the face authentication identical person determination compares the face image photographed at the photographing with the face image read at the storage medium reading, and performs authentication which determines whether the subject is a same person.

14. The alcohol test method of claim 11, further comprising performing communication with an external device in which the face image of the subject preliminarily photographed is registered, and wherein the face authentication identical person determination compares the face image photographed at the photographing with the face image received from the external device, and performs authentication which determines whether the subject is a same person.

15. The alcohol test method of claim 11, wherein, when the result of the authentication indicates that the subject is a same person, and the result of the drinking determination is not in a drunken state, the result controlling outputs a control signal which allows the subject to operate an object system; and wherein, when the result of the authentication indicates that the subject is not a same person, or the result of the drinking determination is in a drunken state, the result controlling outputs a control signal which inhibits the subject from operating the object system.

16. The alcohol test method of claim 11, further comprising a history storage which stores history information in which a date and time when the breath was exhaled at the alcohol testing is associated with the result of the authentication and the result of the drinking determination.

17. The alcohol test method of claim 16,
wherein the result controlling sends out the history information in which the date and time when the breath was exhaled at the alcohol testing is associated with the result of the authentication and the result of the drinking determination.

18. A non-transitory computer-readable storage medium storing a program that causes a computer to perform:
   an alcohol test processing which measures alcohol concentration from breath exhaled by a subject;
   a drinking determination processing which determines whether the subject is in a drunken state based on a measurement result of the alcohol test processing;
   a photograph processing which photographs a face image of the subject by using a trigger that the breath is exhaled at the alcohol test processing such that the face image is photographed responsive to and as a result of exhaling of the breath at the alcohol test processing;
   a face authentication identical person determination processing which compares a face image photographed at the photograph processing with a face image of the subject preliminarily photographed, and performs authentication which determines whether the subject is a same person;
   a result control processing which edits combining a result of authentication by the face authentication identical person determination processing and a result of drinking determination by the drinking determination processing; and
   a result display processing which displays a result edited by the result control processing.

19. The non-transitory computer-readable storage medium of claim 18,
   further causing the computer to perform a face image storage processing in which the face image of the subject preliminarily photographed is registered.

20. The non-transitory computer-readable storage medium of claim 18,
   further causing the computer to perform a storage medium read processing which reads a face image from a storage medium in which the face image of the subject preliminarily photographed is registered,
   wherein the face authentication identical person determination processing compares the face image photographed at the photograph processing with the face image read at the storage medium read processing, and determines whether the subject is a same person.

21. The non-transitory computer-readable storage medium of claim 18,
   further causing the computer to perform a communication processing which communicates with an external device in which the face image of the subject preliminarily photographed is registered,
   wherein the face authentication identical person determination processing compares the face image photographed at the photograph processing with the face image received from the external device, and determines whether the subject is a same person.

22. The non-transitory computer-readable storage medium of claim 18,
   further causing the computer to perform a processing to output a control signal which allows the subject to operate an object system when the result of the identical person authentication indicates that the subject is a same person, and the result of the drinking determination is not in a drunken state; and
   a processing to output a control signal which inhibits the subject from operating the object system when the result of the authentication indicates that the subject is not a same person, or the result of the drinking determination is in a drunken state.

23. The non-transitory computer-readable storage medium of claim 18,
   further causing the computer to perform a history storage processing which stores history information in which a date and time when the breath was exhaled at the alcohol test processing is associated with the result of the authentication and the result of the drinking determination.

24. The non-transitory computer-readable storage medium of claim 23,
   wherein the result control processing causes the computer to perform a processing to send out the history information in which the date and time when the breath was exhaled at the alcohol test processing is associated with the result of the authentication and the result of the drinking determination.

* * * * *